US008883451B2

(12) United States Patent
Gibbs

(10) Patent No.: US 8,883,451 B2
(45) Date of Patent: Nov. 11, 2014

(54) ENHANCED SOLUBLE C5 SACCHARIDE YIELDS

(75) Inventor: Phillip R. Gibbs, Atlanta, GA (US)

(73) Assignee: Renmatix, Inc., King of Prussia, PA (US)

(*) Notice: Subject to any disclaimer, the term of this patent is extended or adjusted under 35 U.S.C. 154(b) by 0 days.

(21) Appl. No.: 13/464,317

(22) Filed: May 4, 2012

(65) Prior Publication Data

US 2012/0282655 A1 Nov. 8, 2012

Related U.S. Application Data

(60) Provisional application No. 61/482,437, filed on May 4, 2011.

(51) Int. Cl.
| | |
|---|---|
| C12P 7/16 | (2006.01) |
| C12P 7/10 | (2006.01) |
| C12P 7/06 | (2006.01) |
| C12P 19/04 | (2006.01) |
| C12P 19/12 | (2006.01) |
| C12P 19/02 | (2006.01) |
| C12P 19/00 | (2006.01) |
| C07H 1/08 | (2006.01) |
| C07H 3/02 | (2006.01) |
| C07H 3/06 | (2006.01) |
| C08H 8/00 | (2010.01) |

(52) U.S. Cl.
CPC ... *C12P 7/16* (2013.01); *C07H 1/08* (2013.01); *C07H 3/02* (2013.01); *C07H 3/06* (2013.01); *C08H 8/00* (2013.01); *C12P 19/02* (2013.01); *C12P 7/065* (2013.01); *C12P 7/10* (2013.01); *C12P 2201/00* (2013.01); *C12P 2203/00* (2013.01); *Y02E 50/10* (2013.01); *Y02E 50/16* (2013.01); *Y02E 50/17* (2013.01)
USPC .............................. 435/72; 127/36

(58) Field of Classification Search
CPC .......... C12P 19/04; C12P 19/12; C12P 19/02; C12P 7/06; C12P 7/10; C12P 19/00; C12P 7/16
See application file for complete search history.

(56) References Cited

U.S. PATENT DOCUMENTS

| | | | |
|---|---|---|---|
| 5,424,417 | A | 6/1995 | Torget et al. |
| 5,705,369 | A | 1/1998 | Torget et al. |
| 5,932,452 | A | 8/1999 | Mustranta et al. |
| 6,022,419 | A | 2/2000 | Torget et al. |
| 6,228,177 | B1 | 5/2001 | Torget |
| 8,057,639 | B2 | 11/2011 | Pschorn et al. |
| 2004/0231661 | A1 | 11/2004 | Griffin et al. |
| 2005/0065336 | A1 | 3/2005 | Karstens |
| 2006/0091577 | A1 | 5/2006 | Shen et al. |
| 2010/0043782 | A1 | 2/2010 | Kilambi |
| 2010/0069626 | A1 | 3/2010 | Kilambi |
| 2010/0170504 | A1 | 7/2010 | Zhang |
| 2010/0203605 | A1 | 8/2010 | Kim et al. |
| 2010/0233771 | A1 | 9/2010 | McDonald et al. |
| 2012/0260912 | A1* | 10/2012 | Nagahama et al. ............. 127/37 |
| 2012/0282656 | A1 | 11/2012 | Gibbs |

FOREIGN PATENT DOCUMENTS

| | | |
|---|---|---|
| CA | 1010859 | 5/1977 |
| CN | 1680415 | 10/2005 |
| CN | 1931866 | 3/2007 |
| CN | 101787398 | 7/2010 |
| CZ | 225851 | 3/1984 |
| CZ | 248106 | 1/1987 |
| EP | 814676 | 1/1998 |
| EP | 1304412 | 4/2003 |
| FR | 2580669 | 10/1986 |
| GB | 1569138 | 6/1980 |
| JP | 04197192 | 7/1992 |
| JP | 2006255676 | 9/2006 |
| JP | 2009077697 A * | 4/2009 |
| JP | 2009189291 | 8/2009 |
| JP | 2010042604 | 2/2010 |
| KR | 20090039470 | 4/2009 |
| WO | 9817727 | 4/1998 |
| WO | 9923260 | 5/1999 |
| WO | 0061276 | 10/2000 |
| WO | 0132715 | 5/2001 |
| WO | 2004013409 | 2/2004 |
| WO | 2006128304 | 12/2006 |
| WO | 2009060126 | 5/2009 |
| WO | 2010045576 | 4/2010 |
| WO | 2010046532 | 4/2010 |
| WO | WO 2010071805 A2 * | 6/2010 |
| WO | 2010102060 | 9/2010 |
| WO | 2011091044 | 7/2011 |

OTHER PUBLICATIONS

Kim ("Plug-Flow Reactor for Continuous Hydrolysis of Glucans and Xylans from Pretreated Corn Fiber." Energy & Fuels, 2005, 19, 2189-2200.*
International Patent Application No. PCT/US2012/036597, "International Search Report and Written Opinion", mailed on Nov. 30, 2012, 10 pages.
Baek et al., "Optimization of the pretreatment of rice straw hemicellulosic hydrolyzates for microbial production of xylitol", Biotechnology and Bioprocess Engineering, 12(4), 2007, 404-9.
Ballesteros et al., "Fractionation of *Cynara cardunculus* (cardoon) biomass by dilute-acid pretreatment", Appl Biochem Biotechnol. Apr. 2007;137-140(1-12):239-52., Apr. 2007, 239-52.
Bustos et al., "Modeling of the hydrolysis of sugar cane bagasse with hydrochloric acid", Applied Biochemistry and Biotechnology, 104(1), 2003, 51-68.
Carrasco et al., (Abstract) "SO2-catalyzed steam pretreatment and fermentation of enzymatically hydrolyzed sugarcane bagasse", Enzyme and Microbial Technology, 46(2), 2010, 64-73.
Carrasco et al., (Abstract) "Effects of dilute acid and steam explosion pretreatments on the cellulose structure and kinetics of cellulosic fraction hydrolysis by dilute acids in lignocellulosic materials", Applied Biochemistry and Biotechnology, 45-46, 1994, 23-34.

(Continued)

*Primary Examiner* — Jon P Weber
*Assistant Examiner* — Charles Zoltan Constantine
(74) *Attorney, Agent, or Firm* — Travis B. Gasa; Ballard Spahr LLP

(57) ABSTRACT

Methods are disclosed for increasing the level of soluble $C_5$ saccharides produced from lignocellulosic biomass comprising acidifying fractionated lignocellulosic biomass to prevent the recondensation of soluble $C_5$ saccharides, including $C_5$ oligosaccharides and xylose and arabinose monomers, to insoluble higher molecular weight $C_5$ oligosaccharides.

64 Claims, 2 Drawing Sheets

(56) References Cited

OTHER PUBLICATIONS

Carvalho et al., (Abstract) "Sugarcane bagasse hydrolysis with phosphoric and sulfuric acids and hydrolysate detoxification for xylitol production", Journal of Chemical Technology and Biotechnology, 79(11), 2004, 1308-1312.

Chen et al., (Abstract) "Study on dilute-acid pretreatment of corn stalk", Linchan Huaxue Yu Gongye, 29(2), 2009, 27-32.

Converti et al., (Abstract) "Wood hydrolysis and hydrolyzate detoxification for subsequent xylitol production", Chemical Engineering & Technology, 23(11), 2000, 1013-1020.

Do Egito De Paiva et al., "Optimization of D-xylose, L-arabinose and D-glucose production obtained from sugar cane bagasse hydrolysis process", Brazilian Symposium on the Chemistry of Lignins and Other Wood Components, 6th, 2001, 333-7.

Dogaris et al., "Hydrothermal processing and enzymatic hydrolysis of sorghum bagasse for fermentable carbohydrates production", Bioresource Technology, 100(24), 2009, 6543-9.

Garrote et al., (Abstract) "Manufacture of xylose-based fermentation media from corncobs by posthydrolysis of autohydrolysis liquors", Applied Biochemistry and Biotechnology, 95(3), 2001, 195-207.

Geddes et al., (Abstract) "Optimizing the saccharification of sugar cane bagasse using dilute phosphoric acid followed by fungal cellulases", Bioresource Technology, 101(6), 2010, 1851-1857.

Harmer et al., (Abstract) "A new route to high yield sugars from biomass: phosphoric-sulfuric acid", Chemical Communications, vol. 43, 2009, 6610-6612.

Herrera et al., (Abstract) "Production of Xylose from Sorghum Straw Using Hydrochloric Acid", Journal of Cereal Science, vol. 37, No. 3, 2003, pp. 267-274.

Jeong et al., (Abstract) "Optimizing dilute-acid pretreatment of rapeseed straw for extraction of hemicellulose", Applied Biochemistry and Biotechnology, 161(1-8), 2010, 22-33.

Karimi et al., "Conversion of rice straw to sugars by dilute-acid hydrolysis", Biomass and Bioenergy, 30(3), 2006, 247-53.

Li et al., (Abstract) "Studies of Monosaccharide Production through Lignocellulosic Waste Hydrolysis Using Double Acids", Energy & Fuels, 22(3), 2008, 2015-2021.

Lloyd et al., (Abstract) "Combined sugar yields for dilute sulfuric acid pretreatment of corn stover followed by enzymatic hydrolysis of the remaining solids", Bioresource Technology, 96(18), 2005, 1967-1977.

Lopez et al., (Abstract) "Chemical characterization and dilute-acid hydrolysis of rice hulls from an artisan mill", BioResources, 5(4), 2010, 2268-2277.

Lu et al., (Abstract) "Optimization of H2SO4-catalyzed hydrothermal pretreatment of rapeseed straw for bioconversion to ethanol: focusing on pretreatment at high solids content", Bioresource Technology, 100(12), 2009, 3048-3053.

McWilliams et al., "Comparison of aspen wood hydrolysates produced by pretreatment with liquid hot water and carbonic acid", Applied Biochemistry and Biotechnology, 98-100, 2002, 109-21.

Neureiter et al., (Abstract) "Dilute acid hydrolysis of presscakes from silage and grass to recover hemicellulose-derived sugars", Bioresource Technology, 92(1), 2004, 21-29.

Neureiter et al., (Abstract) "Dilute-acid hydrolysis of sugarcane bagasse at varying conditions", Applied Biochemistry and Biotechnology, 98-100, 2002, 49-58.

Parajo et al., (Abstract) "Pre-hydrolysis of Eucalyptus wood with dilute sulfuric acid: operation in autoclave", Holz als Roh-und Werkstoff, 52(2), 1994, 102-8.

Pessoa, Jr. et al., (Abstract) "Acid hydrolysis of hemicellulose from sugarcane bagasse", Brazilian Journal of Chemical Engineering, 14(3), 1997, 291-297.

Ramirez et al., (Abstract) "Mathematical modelling of feed pretreatment for bioethanol production", Computer-Aided Chemical Engineering, vol. 26, 2009, 1299-1304.

Roberto et al., (Abstract) "Dilute-acid hydrolysis for optimization of xylose recovery from rice straw in a semi-pilot reactor", Industrial Crops and Products, 17(3), 2003, 171-176.

Sanchez et al., "Dilute-acid hydrolysis for fermentation of the Bolivian straw material Paja Brava", Bioresource Technology, 93(3), 2004, 249-56.

Sarrouh et al., "Biotechnological production of xylitol: enhancement of monosaccharide production by post-hydrolysis of dilute acid sugarcane hydrolysate", Appl Biochem Biotechnol. May 2009;153(1-3), May 2009, 163-70.

Saucedo-Luna et al., "Optimization of acid hydrolysis of bagasse from Agave tequilana Weber", Revista Mexicana de Ingenieria Quimica, 9(1), 2010, 91-7.

Springer, (Abstract) "Prehydrolysis of hardwoods with dilute sulfuric acid", Industrial & Engineering Chemistry Product Research and Development, 24(4), 1985, 614-23.

Strobel et al., "Carbohydrate Transport by the Anaerobic Thermophile *Clostridium thermocellum* LQRI", Applied and Environmental Microbiology, Nov. 1995, 4012-4015.

Trickett et al., (Abstract) "Dilute acid hydrolysis of bagasse hemicellulose", ChemSA, 8(3), 1982, 11-15.

Van Walsum et al., "Carbonic acid enhancement of hydrolysis in aqueous pretreatment of corn stover", Bioresource Technology, 93(3), 2004, 271-226.

Van Walsum, "Severity function describing the hydrolysis of xylan using carbonic acid", Applied Biochemistry and Biotechnology, 91-93, 2001, 317-29.

Varga et al., "Optimization of steam pretreatment of corn stover to enhance enzymatic digestibility", Applied Biochemistry and Biotechnology, 113-116, 2004, 509-23.

Yee et al., "Improvement of xylose production by acid hydrolysis of bagasse pith with low liquor ratio", Report of the Taiwan Sugar Research Institute, Dec. 1982. (98), 1982, 59-70.

Yu et al., "Characteristics and Precipitation of Glucose Oligomers in the Fresh Liquid Products Obtained from the Hydrolysis of Cellulose in Hot-Compressed Water", Ind. Eng. Chem. Res., 2009, 48 (23), pp. 10682-10690, 2009, 10682-90.

Zhang et al., "Cellulose utilization by *Clostridium thermocellum*: Bioenergetics and hydrolysis product assimilation", PNAS, May 17, 2005, 7321-7325.

Zhuang et al., "Research on biomass hydrolysis under extremely low acids by HPLC", Taiyangneng Xuebao, 28(11), 2007, 1239-43.

Bobleter, "Hydrothermal Degradation and Fractionation of Saccharides and Polysaccharides," *Polysaccharides, Structural Diversity and Functional Versatility*, Second Edition, Chapter 40, 2004, 22 pages.

Korean Intellectual Property Office, "International Search Report and Written Opinion" in International Patent Appln. No. PCT/US2012/036605 dated Nov. 30, 2012, 14 pages.

Overend et al., "Fractionation of Lignocellulosics by Steam-Aqueous Pretreatments", *Phil. Trans. R. Soc. Lond. A* vol. 321, 1987, 523-536.

Torget et al., "Optimization of Reverse-Flow, Two-Temperature, Dilute-Acid Pretreatment to Enhance Biomass Conversion to Ethanol", *Applied Biochemistry and Biotechnology*, vol. 57/58, 1996, 85-101.

Um et al., "Acid Hydrolysis of Hemicellulose in Green Liquor Pre-Pulping Extract of Mixed Northern Hardwoods", *Applied Biochemistry and Biotechnology*, 153(1-3), 2009, 127-38.

United States Patent and Trademark Office, "Office Action" in U.S. Appl. No. 13/464,424 mailed May 23, 2013, 21 Pages.

Merriam-Webster ("Suspension" Obtained from www.merriam-webster.com/dictionary/suspension, accessed on Dec. 16, 2013.

Tian et al. "Yeast strains for ethanol production from lignocellulosic hydrosylates during in situ detoxification" Biotechnology Advances (2009) 27, 656-660.

Non-Final Rejection issued Jan. 17, 2014 for U.S. Appl. No. 13/464,424 filed May 4, 2012 and published as US 2012-0282656 on Nov. 8, 2012 (Applicant—Renmatix, Inc.; Inventor—Gibbs; (27 pages).

U.S. Appl. No. 61/482,437, filed May 4, 2011, Phillip R. Gibbs (Renmatix, Inc.).

U.S. Appl. No. 61/482,400, filed May 4, 2011, Phillip R. Gibbs (Renmatix, Inc.).

* cited by examiner

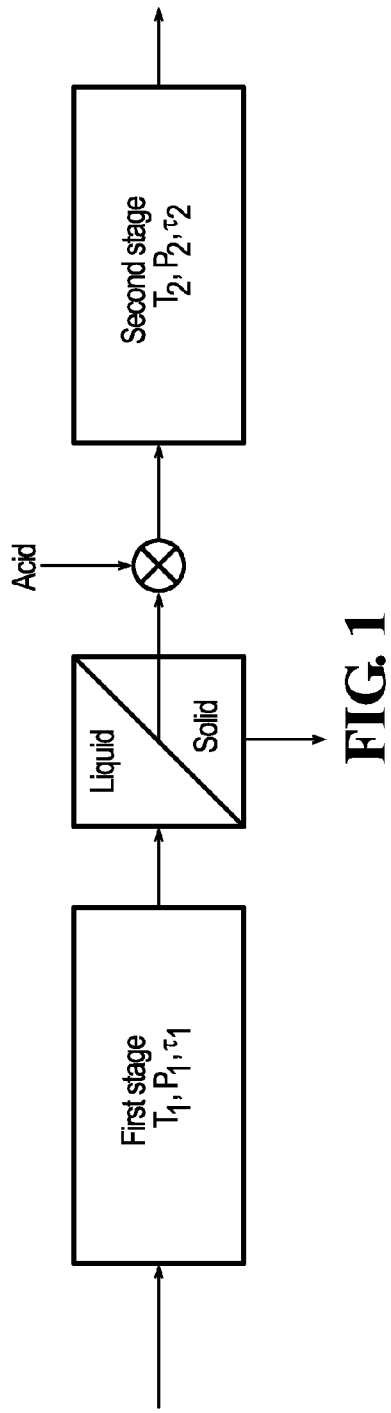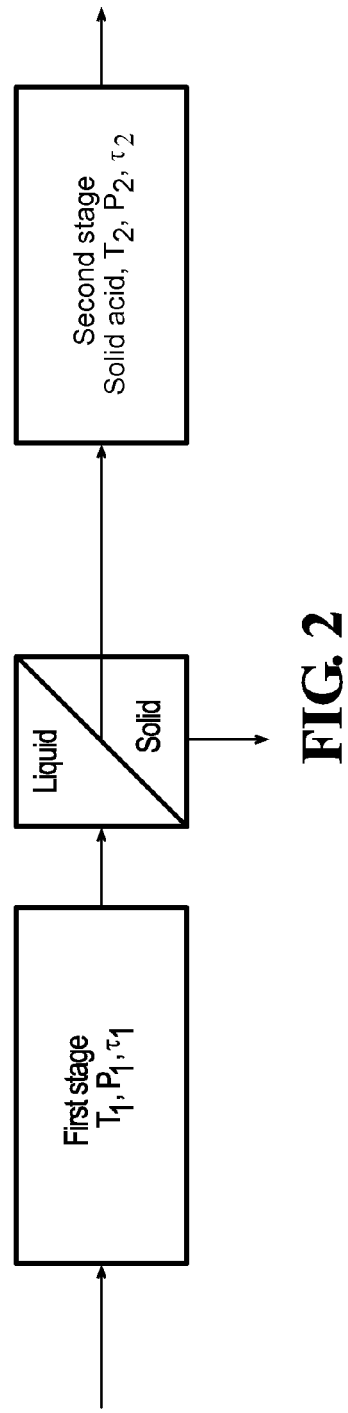

ENHANCED SOLUBLE C5 SACCHARIDE YIELDS

CROSS REFERENCE TO RELATED APPLICATIONS

This application claims benefit to U.S. Application No. 61/482,437 filed May 4, 2011, the entire disclosure of which is incorporated by reference.

FIELD OF THE INVENTION

The present invention generally relates to methods of increasing the yields of fermentable $C_5$ sugars from lignocellulosic biomass. More particularly, it relates to methods of increasing the yields of fermentable $C_5$ sugars from lignocellulosic biomass using steps that maximize monomer formation and minimize the formation of degradation products.

BACKGROUND OF THE INVENTION

There exist methods for converting lignocellulosic biomass into fermentable $C_5$ sugars. Several of these methods first produce oligomers of the $C_5$ sugars, which are then hydrolyzed to form fermentable streams of monomers of $C_5$ sugars. Problems exist with current methods, including, inter alia, that the soluble higher molecular weight oligomers recondense back to insoluble oligomers. To counter this problem, the methods may be performed to drive the hydrolysis of the biomass towards monomer. However, these more stringent conditions often lead to degradation products, such as acids that inhibit fermentation. Also, there are separation challenges as well. It would, therefore, be beneficial to develop methods that avoid this tradeoff to maximize monomer formation and to minimize the formation of degradation products. The methods and compositions of the present invention are directed toward these, as well as other, important ends.

SUMMARY OF THE INVENTION

In one embodiment, the invention is directed to methods of increasing the level of soluble $C_5$ saccharides produced from lignocellulosic biomass, comprising:
  providing a fractionated lignocellulosic biomass comprising:
    a solid fraction comprising:
      optionally, insoluble $C_5$ oligosaccharide;
      cellulose; and
      lignin; and
    a first liquid fraction at a first temperature and a first pressure comprising:
      soluble $C_5$ saccharides selected from the group consisting of $C_5$ oligosaccharides, xylose, arabinose, lyxose, ribose, and mixtures thereof;
      wherein said soluble $C_5$ saccharides are present at a first level;
  acidifying said fractionated lignocellulosic biomass to form a second liquid fraction comprising said soluble C5 saccharides at a second level and at a second temperature;
    wherein said second level is higher than said first level;
    optionally, separating said solid fraction from said second liquid fraction; and
    optionally, hydrolyzing said second liquid fraction to form $C_5$ saccharides selected from the group consisting of $C_5$ oligosaccharides having fewer mer units, $C_5$ monosaccharides, and mixtures thereof.

In another embodiment, the invention is directed to methods of increasing the level of soluble $C_5$ saccharides produced from lignocellulosic biomass, comprising:
  providing a fractionated lignocellulosic biomass comprising:
    a solid fraction comprising:
      optionally, insoluble $C_5$ oligosaccharide;
      cellulose; and
      lignin; and
    a first liquid fraction at a first temperature and a first pressure comprising:
      soluble $C_5$ saccharides selected from the group consisting of $C_5$ oligosaccharides, xylose, arabinose, lyxose, ribose, and mixtures thereof;
      wherein said soluble $C_5$ saccharides are present at a first level;
    optionally, separating said solid fraction from said first liquid fraction at a second pressure;
    wherein said first pressure and said second pressure are substantially the same; contacting said first liquid fraction with a solid acid catalyst to form a second liquid fraction comprising said soluble $C_5$ saccharides at a second level and at a second temperature;
    wherein said second level is greater than said first level;
    optionally, hydrolyzing said second liquid fraction to form $C_5$ saccharides selected from the group consisting of $C_5$ oligosaccharides having fewer mer units, $C_5$ monosaccharides, and mixtures thereof.

In yet other embodiments, the invention is directed to methods of increasing the level of fermentative product or catalytic product produced from lignocellulosic biomass, comprising:
  providing a fractionated lignocellulosic biomass comprising:
    a solid fraction comprising:
      optionally, insoluble $C_5$ oligosaccharide;
      cellulose; and
      lignin; and
    a first liquid fraction at a first temperature and a first pressure comprising:
      soluble $C_5$ saccharides selected from the group consisting of $C_5$ oligosaccharides, xylose, arabinose, lyxose, ribose, and mixtures thereof;
      wherein said soluble $C_5$ saccharides are present at a first level;
  acidifying said fractionated lignocellulosic biomass to form a second liquid fraction comprising said soluble $C_5$ saccharides at a second level and at a second temperature;
    wherein said second level is greater than said first level;
    optionally, separating said solid fraction from said second liquid fraction;
    hydrolyzing said second liquid fraction to form $C_5$ oligosaccharides having fewer mer units, $C_5$ monosaccharides, and mixtures thereof; and
    fermenting, catalyzing, or fermenting and catalyzing said $C_5$ saccharides to form said fermentation product, said catalytic product, or a combination thereof.

In yet other embodiments, the invention is directed to products produced by the methods of the invention.

In yet other embodiments, the invention is directed to compositions, comprising:
  soluble $C_5$ oligosaccharides capable of being membrane separated, preferably having have about 2 mer units to about 15 mer units; and
  water;
  wherein said composition has a pH of about 1.5 to about 6.0; and wherein said soluble C5 oligosaccharides have about 2 mer units to about 15 mer units.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings:

FIG. 1 is a schematic diagram showing the acidification step after separation of the solid fraction from first liquid fraction for one embodiment of the invention.

FIG. 2 is a schematic diagram showing the acidification step using a solid acid catalyst for one embodiment of the invention.

DETAILED DESCRIPTION OF THE INVENTION

Figure 3:
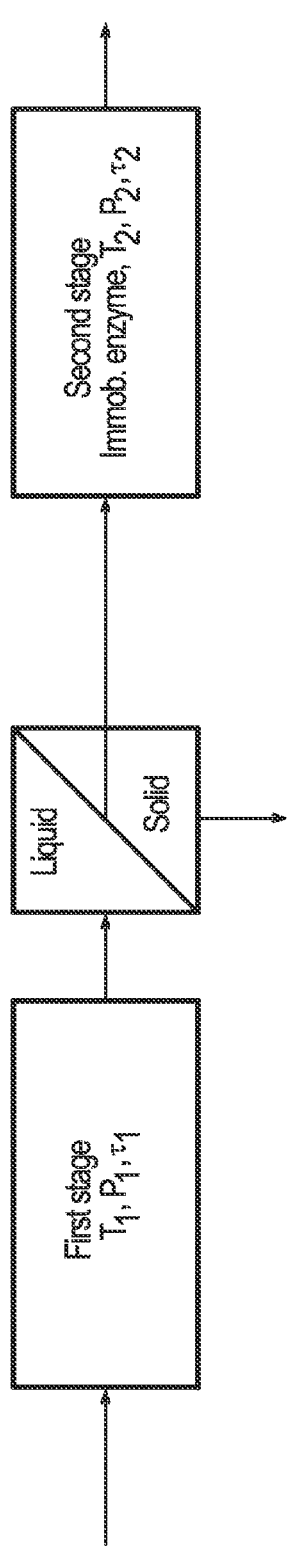
FIG. 3 is a schematic diagram showing the acidification step using an immobilized enzyme for one embodiment of the invention.

As employed above and throughout the disclosure, the following terms, unless otherwise indicated, shall be understood to have the following meanings As used herein, the singular forms "a," "an," and "the" include the plural reference unless the context clearly indicates otherwise.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

A supercritical fluid is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 221 bar; for carbon dioxide, a critical temperature of about 31° C. and a critical pressure of about 72.9 atmospheres (about 1072 psig). Near-critical water has a temperature at or above about 300° C. and below the critical temperature of water (374.2° C.), and a pressure high enough to ensure that all fluid is in the liquid phase. Sub-critical water has a temperature of less than about 300° C. and a pressure high enough to ensure that all fluid is in the liquid phase. Sub-critical water temperature may be greater than about 250° C. and less than about 300° C., and in many instances sub-critical water has a temperature between about 250° C. and about 280° C. The term "hot compressed water" is used interchangeably herein for water that is at or above its critical state, or defined herein as near-critical or sub-critical, or any other temperature above about 50° C. but less than subcritical and at pressures such that water is in a liquid state As used herein, a fluid which is "supercritical" (e.g. supercritical water, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g. water and ethanol, water and $CO_2$, etc). Thus, for example, "a mixture of sub-critical water and supercritical carbon dioxide" indicates a mixture of water and carbon dioxide at a temperature and pressure above that of the critical point for carbon dioxide but below the critical point for water, regardless of whether the supercritical phase contains water and regardless of whether the water phase contains any carbon dioxide. For example, a mixture of sub-critical water and supercritical $CO_2$ may have a temperature of about 250° C. to about 280° C. and a pressure of at least about 225 bar.

As used herein, "continuous" indicates a process which is uninterrupted for its duration, or interrupted, paused or suspended only momentarily relative to the duration of the process. Treatment of biomass is "continuous" when biomass is fed into the apparatus without interruption or without a substantial interruption, or processing of said biomass is not done in a batch process.

As used herein, "resides" indicates the length of time which a given portion or bolus of material is within a reaction zone or reactor vessel. The "residence time," as used herein, including the examples and data, are reported at ambient conditions and are not necessarily actual time elapsed.

As used herein, "lignocellulosic biomass or a component part thereof" refers to plant biomass containing cellulose, hemicellulose, and lignin from a variety of sources, including, without limitation (1) agricultural residues (including corn stover and sugarcane bagasse), (2) dedicated energy crops, (3) wood residues (including sawmill and paper mill discards), and (4) municipal waste, and their constituent parts including without limitation, lignocellulose biomass itself, lignin, $C_6$ saccharides (including cellulose, cellobiose, $C_6$ oligosaccharides, $C_6$ monosaccharides, and $C_5$ saccharides (including hemicellulose, $C_5$ oligosaccharides, and $C_5$ monosaccharides).

In one embodiment, the invention is directed to methods of increasing the level of soluble $C_5$ saccharides produced from lignocellulosic biomass, comprising:

providing a fractionated lignocellulosic biomass comprising:
  a solid fraction comprising:
    optionally, insoluble $C_5$ oligosaccharide;
    cellulose; and
    lignin; and
  a first liquid fraction at a first temperature and a first pressure comprising:
    soluble $C_5$ saccharides selected from the group consisting of $C_5$ oligosaccharides, xylose, arabinose, lyxose, ribose, and mixtures thereof;
    wherein said soluble $C_5$ saccharides are present at a first level;
acidifying said fractionated lignocellulosic biomass to form a second liquid fraction comprising said soluble $C_5$ saccharides at a second level and at a second temperature;
  wherein said second level is greater than said first level;
optionally, separating said solid fraction from said second liquid fraction; and
optionally, hydrolyzing said second liquid fraction to form $C_5$ saccharides selected from the group consisting of $C_5$ oligosaccharides having fewer mer units, xylose, arabinose, lyxose, ribose, and mixtures thereof. The method is shown schematically in FIG. 1.

In another embodiment, the invention is directed to methods of increasing the level of soluble $C_5$ saccharides produced from lignocellulosic biomass, comprising:
providing a fractionated lignocellulosic biomass comprising:
  a solid fraction comprising:
    optionally, insoluble $C_5$ oligosaccharide;
    cellulose; and
    lignin; and
  a first liquid fraction at a first temperature and a first pressure comprising:
    soluble $C_5$ saccharides selected from the group consisting of $C_5$ oligosaccharides, xylose, arabinose, lyxose, ribose, and mixtures thereof;
    wherein said soluble $C_5$ saccharides are present at a first level;
optionally, separating said solid fraction from said first liquid fraction at a second pressure;
  wherein said first pressure and said second pressure are substantially the same;
contacting said first liquid fraction with a solid acid catalyst to form a second liquid fraction comprising said soluble $C_5$ saccharides at a second level and at a second temperature (acidifying step);
  wherein said second level is greater than said first level; and
optionally, hydrolyzing said second liquid fraction to form $C_5$ saccharides selected from the group consisting of $C_5$ oligosaccharides having fewer mer units, xylose, arabinose, lyxose, ribose, and mixtures thereof. The method is shown schematically in FIG. 1.

Figure 4:
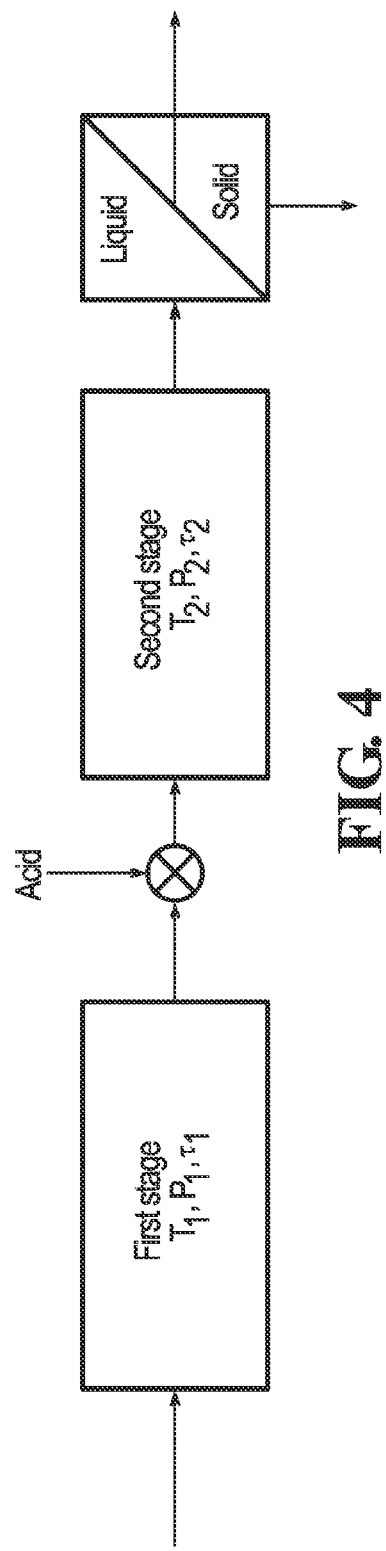
FIG. 4 is a schematic diagram showing the acidification step before the separation of the solid fraction from first fraction for one embodiment of the invention.

In yet other embodiments, the invention is directed to methods of increasing the level of fermentation product or catalytic product produced from lignocellulosic biomass, comprising:
providing a fractionated lignocellulosic biomass comprising:
  a solid fraction comprising:
    optionally, insoluble $C_5$ oligosaccharide;
    cellulose; and
    lignin; and
  a first liquid fraction at a first temperature and a first pressure comprising:
    soluble $C_5$ saccharides selected from the group consisting of $C_5$ oligosaccharides, xylose, arabinose, lyxose, ribose, and mixtures thereof;
    wherein said soluble $C_5$ saccharides are present at a first level;
acidifying said fractionated lignocellulosic biomass to form a second liquid fraction comprising said soluble $C_5$ saccharides at a second level and at a second temperature;
  wherein said second level is greater than said first level;
optionally, separating said solid fraction from said second liquid fraction;
hydrolyzing said second liquid fraction to form $C_5$ saccharides selected from the group consisting of $C_5$ oligosaccharides having fewer mer units, xylose, arabinose, lyxose, ribose, and mixtures thereof; and
fermenting, catalyzing, or fermenting and catalyzing said $C_5$ saccharides to form said fermentation product, said catalytic product, or a combination thereof The acidifying step may be accomplished in a number of ways, including adding an aqueous acid (as shown schematically in FIG. 1 and FIG. 4), contacting with a gaseous compound that forms acid in situ, and/or contacting with a solid acid catalyst (as shown schematically in FIG. 2). The addition of acid hydrolyzes soluble higher molecular weight $C_5$ oligosaccharides and/or insoluble $C_5$ oligosaccharides to form more soluble lower molecular weight $C_5$ oligosaccharides, such that the second level of the soluble $C_5$ saccharides is greater than the first level of the soluble $C_5$ saccharides. The addition of acid shifts MW distribution of soluble higher molecular weight $C_5$ oligosaccharides to a lower average molecular weight, such that the soluble $C_5$ saccharides in second liquid fraction have an average molecular weight that is lower than the average molecular weight of the soluble $C_5$ saccharides in the first liquid fraction. For example, the $C_5$ oligosaccharides in the first liquid fraction have about 2 mer units to about 25 mer units; and the $C_5$ oligosaccharides in the second liquid fraction have about 2 mer units to about 15 mer units.

In certain embodiments, the acidifying step comprises adding to the fractionated lignocellulosic biomass (as shown schematically in FIG. 4) or to the first liquid fraction (as shown schematically in FIG. 1) at least one aqueous acid selected from the group consisting of an organic acid, an inorganic acid, and mixtures thereof. Suitable inorganic acid include, but are not limited to: sulfuric acid, sulfonic acid, phosphoric acid, phosphonic acid, nitric acid, nitrous acid, hydrochloric acid, hydrofluoric acid, hydrobromic acid, hydroiodic acid. Suitable organic acids include, but are not limited to, aliphatic carboxylic acids (such as acetic acid and formic acid), aromatic carboxylic acids (such as benzoic acid and salicylic acid), dicarboxylic acids (such as oxalic acid, phthalic acid, sebacic acid, and adipic acid), aliphatic fatty acids (such as oleic acid, palmitic acid, and stearic acid), aromatic fatty acids (such as phenylstearic acid), and amino acids. In certain embodiments, the acid is preferably sulfuric acid, hydrochloric acid, phosphoric acid, nitric acid, or a combination thereof. Sulfuric acid is especially preferred. In certain embodiments, the acid is present at a level of about 0.05%, by weight, to about 2.0%, by weight, based on the total weight of the fraction to which the acid is added (either fractionated lignocellulosic biomass or first liquid fraction. In certain other embodiments, the amount of acid may be present in an amount from about 0.07% to about 2%, about 0.1% to about 1.5%, about 0.1% to about 1%, about 0.1% to about 0.5%, about 0.1% to about 0.4%, about 0.1% to about 0.3%, about 0.1% to about 0.2%, about 0.5% to about 2%, about 0.5% to about 1.5%, about 0.5% to about 1%, less than about 2%, less than about 1.5%, less than about 1%, less than about 0.5%, less than about 0.4%, less than about 0.3%, less than about 0.2%, or less than about 0.1%.

In certain other embodiments, the acidifying step comprises contacting said fractionated lignocellulosic biomass with a gaseous compound that forms acid in situ. Gaseous compounds that form acid in situ include, but are not limited to, $SO_2$, $CO_2$, $NO_2$, HX (where X is Cl, Br, F, or I), or a combination thereof. In certain embodiments, the acid is present at a level of about 0.05%, by weight, to about 2.0%, by weight, based on the weight of the liquid fraction. In certain other embodiments, the amount of acid may be present in an amount from about 0.07% to about 2%, about 0.1% to about 1.5%, about 0.1% to about 1%, about 0.1% to about 0.5%, about 0.1% to about 0.4%, about 0.1% to about 0.3%, about 0.1% to about 0.2%, about 0.5% to about 2%, about 0.5% to about 1.5%, about 0.5% to about 1%, less than about 2%, less than about 1.5%, less than about 1%, less than about 0.5%, less than about 0.4%, less than about 0.3%, less than about 0.2%, or less than about 0.1%.

In yet other embodiments, the acidifying step comprises contacting said fractionated lignocellulosic biomass with a solid acid catalyst (as shown schematically in FIG. 2). Suitable solid acid catalysts include, but are not limited to, zeolites, cation exchange resins, and combinations thereof.

The methods of the invention are preferably run continuously, although they may be run as batch or semi-batch processes.

The methods of the invention may be carried out in any suitable reactor, including, but not limited to, a tubular reactor, a digester (vertical, horizontal, or inclined), or the like. Suitable digesters include the digester system described in U.S. Pat. No. 8,057,639, which include a digester and a steam explosion unit, the entire disclosure of which is incorporated by reference.

In certain embodiments, the fractionated lignocellulosic biomass is formed by contacting said lignocellulosic biomass with a first reaction fluid comprising hot compressed water and, optionally, carbon dioxide;

wherein said first reaction fluid further comprises acid (either inorganic acid or organic acid, when said lignocellulosic biomass comprises softwood;

wherein said first reaction fluid is at a temperature of at least 100° C. under a pressure sufficient to maintain said first reaction fluid in liquid form.

When the lignocellulosic biomass comprises hardwoods or components other than softwood, the method is preferably carried out without the addition of acid (either inorganic or organic) or formed in situ (other than carbonic acid formed from carbon dioxide). Suitable inorganic acid include, but are not limited to: sulfuric acid, sulfonic acid, phosphoric acid, phosphonic acid, nitric acid, nitrous acid, hydrochloric acid, hydrofluoric acid, hydrobromic acid, hydroiodic acid. Suitable organic acids include, but are not limited to, aliphatic carboxylic acids (such as acetic acid and formic acid), aromatic carboxylic acids (such as benzoic acid and salicylic acid), dicarboxylic acids (such as oxalic acid, phthalic acid, sebacic acid, and adipic acid), aliphatic fatty acids (such as oleic acid, palmitic acid, and stearic acid), aromatic fatty acids (such as phenylstearic acid), and amino acids. In preferred embodiments, the fractionating step is carried out at a temperature no greater than about 240° C. to prevent lignin fouling of the processing equipment. In other preferred embodiments, the fractionating step is carried out without the optional carbon dioxide.

In certain embodiments of the methods, the first temperature and the second temperature are substantially the same. Preferably, the first temperature and said second temperature are both no greater than about 240° C. More preferably, the first temperature and said second temperature are about 220° C. to about 240° C.

In certain embodiments of the methods, the second temperature is less than the first temperature. Preferably, the first temperature and said second temperature are both no greater than about 240° C. More preferably, the first temperature and said second temperature are both no greater than about 180° C.

In certain embodiments, the methods further comprise the step of reducing the first pressure of the first liquid fraction prior to separating the solid fraction from the second liquid fraction.

In certain embodiments, the second liquid fraction is hydrolyzed to form $C_5$ saccharides (oligosaccharides and monosaccharides) enzymatically (as shown schematically in FIG. 3 with immobilized enzyme) or chemically. In certain embodiments, the second liquid fraction is hydrolyzed to form $C_5$ saccharides using, for example, the addition of acid (either inorganic or organic) or formed in situ (other than carbonic acid formed from carbon dioxide). Suitable inorganic acid include, but are not limited to: sulfuric acid, sulfonic acid, phosphoric acid, phosphonic acid, nitric acid, nitrous acid, hydrochloric acid, hydrofluoric acid, hydrobromic acid, hydroiodic acid. Suitable organic acids include, but are not limited to, aliphatic carboxylic acids (such as acetic acid and formic acid), aromatic carboxylic acids (such as benzoic acid and salicylic acid), dicarboxylic acids (such as oxalic acid, phthalic acid, sebacic acid, and adipic acid), aliphatic fatty acids (such as oleic acid, palmitic acid, and stearic acid), aromatic fatty acids (such as phenylstearic acid), and amino acids. using, for example, a dilute acid. In preferred embodiments, the $C_5$ oligosaccharides are contacted with dilute sulfuric acid (at a level of about 0.05% to about 2%, by weight, based on the total weight of the second liquid fraction) for a time sufficient to hydrolyze said $C_5$ oligosaccharides to $C_5$ monosaccharides (xylose, arabinose, lyxose, ribose, or mixtures thereof).

In certain embodiments, the $C_5$ oligosaccharides and monosaccharides (xylose, arabinose, lyxose, ribose, or mixtures thereof) may be fermented to ethanol, butanol, and the like and mixtures thereof, using techniques known to those skilled in the art, including, but not limited to, yeast fermentations using *Saccharomyces cerevisiae* and *Clostridium* sp. In certain preferred embodiments, an oligomer fermentor is able to uptake oligomers directly (generally up to a maximum size, for example, of 6 mer units, for *Clostridium thermocellum*). Thus, by shifting the distribution to oligomers having fewer mer units, the solubility at lower temperatures is enhanced thereby preventing precipitation, but more of the oligomers are accessible to fermentation by organism able to uptake oligomers, such as *Clostridium thermocellum*.

Preferably, the yield of xylose is at least 68%, more preferably, at least 70%, of theoretical yield. Preferably, the yield of the soluble $C_5$ saccharides is at least 68%, more preferably, at least 70%, of theoretical yield.

In certain embodiments, the methods further comprise the step of producing at least one of acetic acid and furfural from said soluble $C_5$ saccharides into at least one of said acetic acid and furfural by conventional methods well known to those in the art. For example, furfural may be produced, for example, by dehydration with an inorganic acid (such as sulfuric acid at pH 1-2) at elevated temperatures (e.g., greater than about 240° C. to about 300° C.) for about 10 seconds. The acetic acid may be released from the hemicellulose in the lignocellulosic biomass.

In certain embodiments, the invention is directed to the products produced by the methods of the invention. In particular, the products are compositions with soluble $C_5$ saccharides having a lower average molecular weight than conventional methods. The methods of the invention lead to soluble oligomers that are less likely to recondense back to insoluble, higher molecular weight oligomers, thereby maximizing monomer formation and minimizing the formation of degradation products. In certain embodiments, the $C_5$ saccharides are preferably maintained as a soluble lower molecular weight oligomers rather than as monosaccharides to permit facile separation. Furfural and formic acid are major degradation products in the dehydration route. Glycolaldehyde, glyceraldehyde, dihydroxyacetone, and pyruvaldehyde, which are products produced via retro-aldol route, are also other possible degradation.

In certain embodiments, the compositions comprise water and soluble $C_5$ oligosaccharides capable of being membrane separated. In certain embodiments, the $C_5$ oligosaccharides have about 2 mer units to about 15 mer units. In certain preferred embodiments, the compositions have a pH of about 1.5 to about 6.0, preferably about 2.0 to about 2.5.

In certain embodiments, the distribution of said $C_5$ oligosaccharides is shifted such that the largest oligomers in the distribution remain soluble at lower temperatures for post processing and separation. For example, it is preferable for purposes for separation to have soluble $C_5$ oligosaccharides rather than monosaccharide because the soluble $C_5$ oligosaccharides may be separated using membrane separation, nanofiltration, and other size exclusion techniques.

While the preferred forms of the invention have been disclosed, it will be apparent to those skilled in the art that various changes and modifications may be made that will achieve some of the advantages of the invention without departing from the spirit and scope of the invention. Therefore, the scope of the invention is to be determined solely by the claims to be appended.

When ranges are used herein for physical properties, such as molecular weight, or chemical properties, such as chemical formulae, all combinations, and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of producing soluble $C_5$ saccharides from lignocellulosic biomass, comprising:
   providing a fractionated lignocellulosic biomass comprising:
     a solid fraction comprising:
       optionally, insoluble $C_5$ oligosaccharide;
       cellulose; and
       lignin; and
     a first liquid fraction at a first temperature and a first pressure comprising:
       soluble $C_5$ saccharides selected from the group consisting of $C_5$ oligosaccharides, xylose, arabinose, lyxose, ribose, and mixtures thereof;
       wherein said soluble $C_5$ saccharides are present at a first level;
   optionally, separating said solid fraction from said first liquid fraction at a second pressure;
   contacting said first liquid fraction with a solid acid catalyst to form a second liquid fraction comprising said soluble $C_5$ saccharides at a second level and at a second temperature;
     wherein said second level is greater than said first level; and
     wherein said second temperature is less than said first temperature;
   optionally, hydrolyzing said second liquid fraction to form $C_5$ saccharides selected from the group consisting of $C_5$ oligosaccharides having fewer mer units, xylose, arabinose, lyxose, ribose, and mixtures thereof;
   wherein said fractionated lignocellulosic biomass is formed by contacting said lignocellulosic biomass with a first reaction fluid comprising hot compressed water and, optionally, carbon dioxide;
   wherein said first reaction fluid further comprises acid, when said lignocellulosic biomass comprises softwood; and
   wherein said first reaction fluid is at a temperature of at least 100° C. under a pressure sufficient to maintain all of said first reaction fluid in liquid form.

2. A method of claim 1,
   wherein said solid acid catalyst is a zeolite, a cation exchange resin, or a combination thereof.

3. A method of claim 2,
   wherein said solid acid catalyst is a zeolite.

4. A method of claim 2,
   wherein said solid acid catalyst is a cation exchange resin.

5. A method of claim 1,
   wherein said method is continuous.

6. A method of claim 1,
   wherein said soluble $C_5$ saccharides in said second liquid fraction have an average molecular weight that is lower than the average molecular weight of said soluble $C_5$ saccharides in said first liquid fraction.

7. A method of claim 1,
   wherein said $C_5$ oligosaccharides in said first liquid fraction have about 2 mer units to about 25 mer units; and
   wherein said $C_5$ oligosaccharides in said second liquid fraction have about 2 mer units to about 15 mer units.

8. A method of claim 1,
   wherein said first temperature and said second temperature are both no greater than about 240° C.

9. A method of claim 1,
   wherein said separating is performed; and
   wherein said first pressure is reduced prior to said separating.

10. A method of claim 1,
   wherein said hydrolyzing said second liquid fraction to form $C_5$ saccharides is performed and comprises contacting said $C_5$ oligosaccharides with dilute acid for a time sufficient to hydrolyze said $C_5$ oligosaccharides to $C_5$ oligosaccharides having fewer mer units, xylose, arabinose, lyxose, ribose, and mixtures thereof.

11. A method of claim 10,
   wherein said dilute acid is sulfuric acid.

12. A method of claim 11,
   wherein said sulfuric acid is present at a level of about 0.05 wt. % to about 2 wt. %, based on the total weight of the second liquid fraction.

13. A method of claim 1,
   wherein said hydrolyzing said second liquid fraction to form $C_5$ saccharides is performed and comprises enzymatic hydrolysis.

14. A method of claim 1,
wherein the yield of said xylose is at least 68% of theoretical yield.
15. A method of claim 1,
wherein the yield of said soluble $C_5$ saccharides is at least 68% of theoretical yield.
16. A method of claim 1, further comprising:
producing at least one of acetic acid and furfural from said soluble $C_5$ saccharides.
17. A method of claim 16,
wherein furfural is produced from said soluble $C_5$ saccharides by dehydration with an inorganic acid.
18. A method of claim 17,
wherein said dehydration is performed at a temperature of about 240° C. to about 300° C.
19. A method of claim 17,
wherein said inorganic acid is sulfuric acid.
20. A method of claim 1,
wherein said first pressure and said second pressure are substantially the same.
21. A method of claim 1,
wherein said method is carried out in a digester.
22. A method of claim 21,
wherein said digester is a vertical digester.
23. A method of claim 1,
wherein said method is carried out in a digester system comprising a digester and a steam explosion unit.
24. A method of claim 1,
wherein said contacting said first liquid fraction with a solid acid catalyst further comprises adding an aqueous acid.
25. A method of claim 24,
wherein said aqueous acid is selected from the group consisting of sulfuric acid, phosphoric acid, nitric acid, and hydrochloric acid.
26. A method of claim 24,
wherein said aqueous acid is sulfuric acid.
27. A method of claim 24,
wherein said aqueous acid is present in an amount from about 0.07 wt. % to about 2 wt. %.
28. A method of claim 24,
wherein said aqueous acid is present in an amount of less than about 1 wt. %.
29. A method of claim 24,
wherein said aqueous acid is present in an amount of less than about 0.5 wt. %.
30. A method of claim 1,
wherein said contacting said first liquid fraction with a solid acid catalyst further comprises adding a gaseous compound that forms acid in situ.
31. A method of claim 30,
wherein said gaseous compound is selected from the group consisting of $SO_2$, $CO_2$, $NO_2$, HX, or a combination thereof; and
wherein X is Cl, Br, F, or I.
32. A method of claim 30,
wherein said gaseous compound is $SO_2$.
33. A method of claim 30,
wherein said gaseous compound is $CO_2$.
34. A method of claim 30,
wherein said gaseous compound is present in an amount of about 0.07 wt. % to about 2 wt. %.
35. A method of claim 30,
wherein said gaseous compound is present in an amount of less than about 1 wt. %.
36. A method of claim 30,
wherein said gaseous compound is present in an amount of less than about 0.5 wt. %.
37. A method of claim 1,
wherein said method is performed as a batch process.
38. A method of claim 1,
wherein said method is performed as a semi-batch process.
39. A method of claim 1,
wherein said hydrolyzing said second liquid fraction to form $C_5$ saccharides is performed and comprises addition of an acid selected from the group consisting of sulfonic acid, phosphoric acid, phosphonic acid, nitric acid, nitrous acid, hydrochloric acid, hydrobromic acid, hydroiodic acid, acetic acid, formic acid, benzoic acid, salicylic acid, oxalic acid, and adipic acid.
40. A method of claim 39,
wherein said acid is phosphoric acid.
41. A method of claim 39,
wherein said acid is nitric acid.
42. A method of claim 39,
wherein said acid is acetic acid.
43. A method of claim 39,
wherein said acid is oxalic acid.
44. A method of claim 1,
wherein said hydrolyzing said second liquid fraction to form $C_5$ saccharides is performed.
45. A method of claim 44,
further comprising separating said $C_5$ oligosaccharides having fewer mer units using membrane separation.
46. A method of claim 44,
further comprising separating said $C_5$ oligosaccharides having fewer mer units using nanofiltration.
47. A method of claim 1,
further comprising fermenting said soluble $C_5$ saccharides in said second liquid fraction to produce ethanol, butanol, or mixtures thereof.
48. A method of claim 47,
wherein said fermenting produces ethanol.
49. A method of claim 47,
wherein said fermenting produces butanol.
50. A method of claim 1,
further comprising separating $C_5$ oligosaccharides present in said second liquid fraction using membrane separation.
51. A method of claim 1,
further comprising separating $C_5$ oligosaccharides present in said second liquid fraction using nanofiltration.
52. A method of claim 1,
wherein said first reaction fluid further comprises carbon dioxide.
53. A method of claim 1,
wherein said lignocellulosic biomass comprises hardwood.
54. A method of claim 53,
wherein said fractionated lignocellulosic biomass is prepared without the addition of acid.
55. A method of claim 1,
wherein said lignocellulosic biomass comprises softwood.
56. A method of claim 55,
wherein said acid in said first reaction fluid comprises an inorganic acid.
57. A method of claim 56,
wherein said inorganic acid is selected from the group consisting of sulfuric acid, phosphoric acid, nitric acid, and hydrochloric acid.
58. A method of claim 56,
wherein said inorganic acid is sulfuric acid.

59. A method of claim 56,
wherein said inorganic acid is phosphoric acid.

60. A method of claim 55,
wherein said acid in said first reaction fluid comprises an organic acid.

61. A method of claim 60,
wherein said organic acid is selected from the group consisting of acetic acid, formic acid, benzoic acid, salicylic acid, oxalic acid, and an amino acid.

62. A method of claim 60,
wherein said organic acid is oxalic acid.

63. A method of claim 60,
wherein said organic acid is acetic acid.

64. A method of claim 60,
wherein said organic acid is formic acid.

* * * * *